United States Patent
Johnson et al.

(10) Patent No.: US 8,722,333 B2
(45) Date of Patent: May 13, 2014

(54) GSTP1 AS TERATOGENIC ALLELE FOR AUTISM AND ASSAYS AND METHODS BASED THEREON

(75) Inventors: William G. Johnson, Short Hills, NJ (US); Edward S. Stenroos, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 553 days.

(21) Appl. No.: 12/449,933

(22) PCT Filed: Mar. 6, 2008

(86) PCT No.: PCT/US2008/003052
§ 371 (c)(1),
(2), (4) Date: Feb. 4, 2010

(87) PCT Pub. No.: WO2008/109147
PCT Pub. Date: Sep. 12, 2008

(65) Prior Publication Data
US 2010/0143318 A1    Jun. 10, 2010

Related U.S. Application Data

(60) Provisional application No. 60/905,135, filed on Mar. 6, 2007.

(51) Int. Cl.
*C12Q 1/68* (2006.01)
*C12P 19/34* (2006.01)

(52) U.S. Cl.
USPC ............................ 435/6.12; 435/6.1; 435/6.11

(58) Field of Classification Search
None
See application file for complete search history.

(56) References Cited

PUBLICATIONS

Serajee et al., "Polymorphisms in Xenobiotic Metabolism Genes and Autism," Journal of Child Neurobiology, Jun. 2004, vol. 19, No. 6, pp. 413-417.*

* cited by examiner

*Primary Examiner* — Young J Kim
(74) *Attorney, Agent, or Firm* — Fox Rothschild LLP

(57) ABSTRACT

The present invention provides novel markers and assays for autism based on the association of GSTP1 with prevalence for having a child or children with autism or autistic disease. The invention relates to the use and application of GSTP1 as a susceptibility marker and teratogenic allele for autism. In particular the genotype of GSTP1 at amino acids 105 and 114, corresponding to nucleotides 313 and 341 are determined. GSTP1 may be combined with other markers in methods and assays for monitoring, managing, diagnosis, prenatal diagnosis, and assessment of autism. In addition, the present invention discloses a novel method for identifying individuals who are genetically susceptible to have offspring with autism wherein the genotype of GSTP1, alone or in combination with other genetic markers or other indicators of oxidative stress, is determined.

6 Claims, No Drawings

US 8,722,333 B2

GSTP1 AS TERATOGENIC ALLELE FOR AUTISM AND ASSAYS AND METHODS BASED THEREON

CROSS REFERENCE TO RELATED APPLICATIONS

The present application claims priority of co-pending provisional application U.S. Ser. No. 60/905,135, filed on Mar. 6, 2007, the disclosure of which is incorporated by reference herein in its entirety. Applicants claim the benefits of such application under 35 U.S.C. §119(e).

FIELD OF THE INVENTION

This invention relates to a glutathione S-transferase P1 haplotype, which, acting in mothers during pregnancy, may increase risk of autistic disorder in her offspring. The present invention relates generally to markers and assays for autism and to the association of GSTP1 with autism as a maternal marker exerting maternal effects, particularly as a teratogenic allele for autism. GSTP1 may be combined with other markers in methods and assays for diagnosis, prenatal diagnosis, prenatal monitoring, and assessment of autism. The GSTP1 pathway and its associated proteins provide targets for therapeutic intervention in prevention, modulation, or therapy of autism.

BACKGROUND OF THE INVENTION

Autism (autistic disorder) is a pervasive developmental disorder with diagnostic criteria based on abnormal social interactions, language abnormalities, and stereotypies evident prior to 36 months of age. Despite its lack of Mendelian transmission autism is highly genetically determined.

In most cases in which a gene has been associated with a disorder, the disease allele acts in the affected individual. Alternatively, a disease allele of a gene may act in the mother during pregnancy to contribute to the phenotype of her affected child[1]. So far, there is evidence for such maternally acting alleles, so-called teratogenic alleles, for only a handful of genes (reviewed in Johnson W G, 2003[2]).

Examples of teratogenic alleles include: (1) in spina bifida, the G-allele of the MTR A2756G, the G-allele of the MTRR polymorphisms[3] and the deletion allele of the DHFR 19 bp deletion polymorphism[4]; (2) in Down syndrome, the G-allele of the MTRR A66G and T-allele of the MTHFR C677T polymorphisms[5]; (3) in orofacial clefting, the GSTT1-null allele homozygotes[6]. Demonstrating increased frequency of a putative teratogenic allele in mothers but not fathers of affected individuals is evidence for a teratogenic allele and is the method that has been used in most reports. Strong evidence of a teratogenic allele, e.g. by maternal transmission disequilibrium testing (TDT) has rarely been achieved[3], and there is strong evidence for none so far in autism.

Children with autistic disorder (AD) show deviation from the normal developmental pattern with impaired social interactions and communication, restricted interests, and repetitive, stereotyped patterns of behaviour that are evident prior to 36 months of age[7,8]. Clinical genetic studies and modelling studies suggest that AD may be caused by multiple interacting gene loci[9,10] while environmental and epigenetic factors may contribute to variable expressivity possibly through interaction with genetic susceptibility factors[10,11]. Environmental factors contributing to AD could include toxic endogenous metabolites or exogenous toxins or teratogens.

Neuropathological studies[12,13], cytoarchitectonic studies[14], minicolumn studies[15,16] and neonatal blood studies of neurotrophins and neuropeptides[17] all support the prenatal origin of certain brain abnormalities in autism. Consequently, it is possible that maternal genes, acting during pregnancy, could contribute to the autism phenotype in the fetus.

A number of maternal effects have been described for autism, but none reported so far gives strong evidence of a teratogenic allele. For some of these no involvement of specific maternal genes have yet been demonstrated, e.g., autism associated with maternal ingestion during pregnancy of thalidomide[18] or valproic acid[19] and increased risk of autism spectrum disorder in children of mothers with diabetes or epilepsy[20]. There is some evidence that maternal alleles at the MAO-A locus and possibly the DBH locus may modify IQ in children with autism[21]. Diminished IQ is often seen in autism, though not as a cardinal feature. Although mental retardation is not part of the diagnostic criteria for autism, the two diagnoses could be interacting through diagnostic substitution in the population[22]. In addition, some alleles of the glutamate receptor 6 (GluR6, GRIK2) reportedly showed increased maternal transmission to male children with autism[23]; these findings were ascribed to meiotic drive or imprinting. There is evidence that the major histocompatibility complex (MHC) extended haplotype, HLA B44-SC30-DR4, may act as a teratogenic allele for autism since the frequency of this haplotype was increased in mothers of autism cases compared with controls[24]. So far, this has not been confirmed with a stronger study design such as maternal TDT. This haplotype frequency was also increased in autism cases compared with controls suggesting action in the cases as well[24].

Some recent studies in humans have linked oxidative stress to autism[25]. For example, significantly decreased levels of glutathione (GSH), significantly lower ratio of reduced GSH to oxidized GSH, and other metabolic abnormalities in individuals with autism were interpreted as evidence of oxidative stress[26,27]. Glutathione is the most important endogenous antioxidant[28] and is the most abundant non-protein thiol[29]. Recently, increased urinary excretion of 8-isoprostane-F2α, a biomarker of lipid peroxidation and oxidative stress, was found in autism[30], a finding that has been confirmed[31].

Accumulating data support the importance of the glutathione S-transferase (GST) supergene family as one of the factors protecting against reactive oxygen species and the products of oxidative stress[32,33]. GSTs, one category of Phase II enzymes[34], catalyze the conjugation of GSH to a variety of toxic electrophiles that have been activated by phase I enzymes. GSTs conjugate and detoxify products of oxidative stress. GSTs also conjugate toxins that produce oxidative stress[35]. Sometimes, conjugation of GSH to a compound by GST can increase its toxicity or even create toxicity[36].

Seven cytosolic families of GSTs are known in humans, including at least 16 cytosolic GST subunits (most of them polymorphic), with some alleles causing functional alteration. For alleles with diminished function, their specific substrates might accumulate and contribute to oxidative damage; increased enzyme activity could also lead to oxidative damage; increased enzyme activity could also lead to oxidative damage if the product is toxic.[35] The pi class of GSTs, represented by a single GST (variously known as GSTP1, GSTP1-1, GSTP, GSTp, and GSTpi) coded for by a gene on chromosome 11q13, is expressed at the highest levels in most extrahepatic tissues.[36]

GSTP1 has 4 recognized polymorphic alleles, designated *A, *B, *C, and *D. These alleles result from 2 amino acid changes: Ile105Val (A313G) and Ala114Val (C341T). There is evidence[37,38] that these polymorphic variants are functional, affecting enzyme activity and substrate specificity. For example, variation at position 105 affects thermostability of the GSTP1 enzyme[39] and its catalytic efficiency for some substrates[39,40] and correlates with oxidative DNA damage in breast cancer tissues.[41]

There remains a need for methods and assays to determine susceptibility to and provide diagnostic markers associated with autism. Improved methods and additional relevant autism genetic markers are therefore needed. Further, identification of relevant and novel targets for intervention and therapy to prevent, alleviate, and modulate autism is needed.

The citation of references herein shall not be construed as an admission that such is prior art to the present invention.

SUMMARY OF THE INVENTION

The invention relates generally to the identification and characterization of an enzyme involved in detoxification and its variant allele(s) linked with increased oxidative stress as a maternal marker and teratogenic allele for autism and autistic disorders. The invention relates to the identification and characterization of GSTP1 as a maternal marker and teratogenic allele for autism and autistic disorders. In particular, a GSTP1 allele has been found to have a significant association in the mother with autism in her fetus or child (ren). GSTP1 has been found to exert maternal effects acting as a teratogenic allele for autism. In particular, a GSTP1 polymorphism that affects thermostability, catalytic efficiency and correlates with oxidative DNA damage has been identified as a maternal marker and teratogenic allele. Thus, alterations in the detoxification pathway or increased oxidative stress or DNA damage in a pregnant mother can result in an increased risk for or susceptibility to autism in the fetus. GSTP1 genotyping, particularly in combination with other genes or markers associated with oxidative stress or autism, may be utilized in tests, assays, methods, kits for diagnosing, predicting, modulating, or monitoring autism, including maternal assessment and monitoring, susceptibility assessment, carrier testing and prenatal diagnosis. Alterations in oxidative stress or detoxification pathway enzymes, including that of GSTP1 and other pathway enzymes, may be assessed and monitored in a pregnant woman or other family members to determine risk for or susceptibility to autism in a fetus. Management of oxidative stress in a pregnant woman with an altered enzyme may, therefore, reduce likelihood of autism in her at risk fetus.

Therefore, the present invention provides methods of identifying a mother with an increased likelihood for having an autistic child or identifying an individual as being genetically susceptible to having or developing autism or an autistic disorder. The present invention further provides methods of identifying an individual as being genetically susceptible for having offspring that are susceptible for developing autism or an autistic disorder. Methods of identifying an individual as being susceptible due to genetic or environmental factors for having or developing autism are also provided. The present invention also provides methods of identifying an individual, particularly a mother, as being likely to have a child which is susceptible for having or developing an autistic disorder due to both environmental and genetic factors, particularly wherein assessment of the GSTP1 genotype of the mother is made and the result is incorporated in the method.

The present invention therefore provides methods for compiling genetic datasets which include the GSTP1 genotype of an individual or individuals for use in determining a predicted probability for an individual of having a child with susceptibility for having or developing autism, or for having offspring that develop autism.

The present invention extends to diagnostic assays, kits and methods for determining the GSTP1 genotype of a subject, thereby providing a means to diagnosing or determining susceptibility in a mother for having offspring with increased likelihood of autism or autism disorders.

In accordance with the present invention, a diagnostic assay is provided for determining susceptibility to having a child with autism in a mother which comprises (a) isolating nucleic acid from said mother; and (b) characterizing the GSTP1 genotype, thereby determining the mother's susceptibility for having an offspring with autism.

The present invention also provides for the use of the nucleic acids of GSTP1 in the methods of the present invention for identifying, diagnosing, or predicting in a mother an increased likelihood of having a child with autism and for modulating, monitoring, preventing and/or treating individuals with autism or a suspected prevalence for autism, including treatment of a fetus in utero.

Determining if the biological sample contains the genetic variant of GSTP1, particularly identifying the GSTP1 alleles or variants, can be performed by any appropriate method including, but not limited to PCR, special PCR, RT PCR, RFLP analysis, SSCP, oligonucleotide hybridization, base extension and FISH. Accordingly, it is a principal object of the present invention to provide a method for identifying a mother with increased likelihood to have an autistic child or a child, including a fetus, that is genetically inclined or teratogenically susceptible to develop autism or autistic disease.

It is a further object of the present invention to provide a method for identifying an individual that is genetically inclined to have offspring having autistic disease.

It is a further object of the present invention to provide a method of determining susceptibility in a mother for having a child with autism. It is a further object to provide a method for modulating autism or modifying the likelihood of developing autism in a fetus by monitoring and managing teratogenic effects in the mother. The method utilizes the determination of the GSTP1 genotype to determine susceptibility to autism and to monitor and manage teratogenic effects for autism.

In an aspect of the method the GSTP1 allele is determined. In a particular such aspect the GSTP1 allele of an individual is determined as selected from at least *A, *B, *C or *D. In a further aspect of the method, the GSTP1 genotype at amino acids 105 and 114, corresponding to nucleic acids 313 and 341, respectively, is determined. In a further particular aspect, it is determined whether GSTP1 nucleotide 313 is an A or a G, and it is determined whether GSTP1 nucleotide 341 is a C or a T.

In an additional aspect of the method, the genotype for the gene GSTP1 is determined by PCR analysis. In one such aspect, PCR analysis is combined with RFLP analysis.

The invention provides a method for determining the susceptibility of a mother to having offspring that is at risk of developing autism comprising:

(a) collecting a biological sample from one or more participants; wherein a participant is the mother; and wherein the biological sample contains nucleic acids and/or proteins of the participant; and (b) analyzing the nucleic acids and/or proteins from the biological sample;

wherein said analyzing results in a genotype for the gene GSTP1;

wherein the susceptibility of a mother to having offspring at increased risk to develop autism is estimated.

In one aspect of the invention, step (b) comprises performing PCR amplification of GSTP1 to determine the genotype at nucleic acid 313. In a further aspect, step (b) further comprises performing PCR amplification of GSTP1 to determine the genotype at nucleic acid 341. In a further aspect of the method, in step (b), the amplified GSTP1 nucleic acid is restricted with a restriction enzyme. In one embodiment, the step (b) comprises performing PCR amplification of GSTP1 to determine the genotype at nucleotide 313 using primers of SEQ ID NO: 1 and 2, and performing PCR amplification of GSTP1 to determine the genotype at nucleotide 341 using primers of SEQ ID NO: 3 and 4. In this embodiment, the amplified nucleotide 313 region nucleic acid is cleaved with restriction enzyme Alw26I, and the amplified nucleotide 341 region nucleic acid is cleaved with restriction enzyme AciI. In an alternative method, the step (b) comprises performing PCR amplification of GSTP1 to determine the genotype at nucleotide 313 using primers of SEQ ID NO: 5 and 6, and performing PCR amplification of GSTP1 to determine the genotype at nucleotide 341 using primers of SEQ ID NO: 7 and 8. In this embodiment, the amplified nucleotide 313 region nucleic acid is cleaved with restriction enzyme Alw26I, and the amplified nucleotide 341 region nucleic acid is cleaved with restriction enzyme AciI.

The invention further provides an assay for determining susceptibility to having autistic offspring in a woman or a mother which comprises:

(a) isolating nucleic acid from said woman or mother; and
(b) characterizing the GSTP1 genotype, thereby determining the susceptibility for having autistic offspring of said woman or mother.

In an embodiment of the assay, the genotype for the gene GSTP1 is determined by PCR analysis. In one such aspect, PCR analysis is combined with RFLP analysis. PCR analysis may be performed with combinations of primers of SEQ ID NO: 1 and 2 or SEQ ID NO: 5 and 6 for the Ile105Val (A313G) allele and/or combinations of primers of SEQ ID NO: 3 and 4 or SEQ ID NO: 7 and 8 for the Ala114Val (C341T) allele.

The invention provides a method of estimating the susceptibility of an individual to have offspring that develop a developmental disorder comprising:

(a) collecting a biological sample from one or more participants; wherein a participant is either the individual or a blood relative of the individual; and wherein the biological sample contains nucleic acids and/or proteins of the participant;
(b) analyzing the nucleic acids and/or proteins from the biological sample;
wherein said analyzing results in a genotype for the gene GSTP1; and wherein said genotype forms a partial or full dataset of genetic explanatory variables for the participants; and
(e) analyzing the dataset;
wherein the susceptibility of an individual to have offspring that develop autism is estimated.

In a further embodiment of the method, the GSTP1-313 and GSTP1-341 genotype is determined. In one embodiment, the GSTP1-313 genotype is determined. In a further embodiment, the genotype for the gene GSTP1 is determined by PCR analysis. The GSTP1-313 genotype may be determined using PCR primers SEQ ID NO: 1 and 2. The GSTP1-341 genotype may be determined using PCR primers SEQ ID NO: 3 and 4.

The present invention includes a test kit for assessing susceptibility to autism in a subject or in an offspring, comprising nucleic acid probes or primers for determining the GSTP1 genotype of said subject or of said offspring's parents, particularly the offspring's mother, during pregnancy. The test kit may comprise primers or probes for determining the GSTP1-313 and GSTP1-341 genotype. The test kit may comprise nucleic acid primers or probes selected from SEQ ID NO: 1 and 2 and SEQ ID NO: 3 and 4.

Other objects and advantages will become apparent to those skilled in the art from a review of the following description which proceeds with reference to the following illustrative drawings.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the terms shall have the definitions set out below. The terms "glutathione S-transferase P1", "glutathione S-transferase pi", "GST P1", "GSTP", "GSTpi" and any variants not specifically listed, may be used herein interchangeably, and as used throughout the present application and claims refer to proteins, polypeptides and enzymes, and extends to those nucleic acids encoding said polypeptides, including the upstream and downstream and flanking nucleic acid sequences, including any genetic variants, mutants, and/or null mutants thereof.

Accordingly, proteins and nucleic acids displaying substantially equivalent or altered activity or derived from the GSTP1 chromosomal locus or from GSTP1 mRNA are likewise contemplated. These modifications may be deliberate, for example, such as modifications obtained through site-directed mutagenesis, or may be natural variants or accidental, such as those obtained through variations or mutations in mammals including humans or in hosts that are producers of the enzyme. Also, the terms "glutathione S-transferase P1", "glutathione S-transferase pi", "GSTP", "GSTP", "GSTpi" are intended to include within their scope proteins specifically recited herein as well as all substantially homologous analogs and allelic variations.

Cytosolic and membrane-bound forms of glutathione S-transferase are encoded by two distinct supergene families. Eight distinct classes of the soluble cytoplasmic mammalian glutathione S-transferases have been identified: alpha, kappa, mu, omega, pi, sigma, theta and zeta. The GSTP1 gene encodes a glutathione S-transferase that belongs to the pi class. The pi class of enzymes functions in the detoxification of electrophilic compounds, including carcinogens, therapeutic drugs, environmental toxins and products of oxidative stress, by conjugation with glutathione. The gene encoding the pi class of GST is found on chromosome 11q13. Genetic variations in GST genes, including GSTP1, can change an individual's susceptibility to carcinogens and toxins as well as affect the toxicity and efficacy of certain drugs. Mutations in the GSTP1 gene have been linked with an increase in a number of cancers, likely due to an increased susceptibility to environmental toxins and carcinogens, and to lung disease and asthma. (Harries, L W, Stubbins, M J, Forman, D, Howard, G C W and Wolf, C R (1997) Carcinogenesis 18(4): 641-644; Aynacioglu, A S, Nacak, M, Filiz, A, Ekinci, E and Roots, I (2003) Br J Clin Pharmacol 57(2):213-217; Watson, M A, Stewart, R K, Smith, G B J, Massey, T E and Bell, D A (1998) Carcinogenesis 19(2):275-280). The GSTP1 nucleic acid and protein sequence from humans and various other species are publicly known. Human GSTP1 mRNA sequences are set out, for instance, in Genbank entries NM_000852 and DQ 895985. Complete human GSTP1 coding sequence is provided in Genbank entry BC010915. Exemplary human GSTP1 amino acid sequence is set out in SEQ ID NO:9 and nucleic acid sequence is set out in SEQ ID NO:10.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

An "upstream regulatory region" is a DNA regulatory region capable of binding RNA polymerase in a cell and initiating transcription of a downstream (3' direction) coding sequence. For purposes of defining the present invention, the upstream regulatory region sequence is bounded at its 3' terminus by the transcription initiation site and extends upstream (5' direction) to include the minimum number of bases or elements necessary to initiate transcription at levels detectable above background and under appropriate regulatory control. Within the upstream regulatory region sequence will be found a transcription initiation site (conveniently defined by mapping with nuclease S1), as well as protein binding domains (consensus sequences) responsible for the binding of RNA polymerase and regulatory regions (consensus sequences) responsible for appropriate regulatory control, including cellular expression, induction of expression, etc. Eukaryotic promoters will often, but not always, contain "TATA" boxes and "CAT" or "CATA" boxes.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 10 or more nucleotides, preferably 15-25 nucleotides, although it may contain fewer nucleotides or more nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, "pg" means picogram, "ng" means nanogram, "ug" or "μg" mean microgram, "mg" means milligram, "ul" or "μl" mean microliter, "ml" means milliliter, "l" means liter.

A labeled oligonucleotide or primer may be utilized in the methods, assays and kits of the present invention. The labeled oligonucleotide may be utilized as a primer in PCR or other method of amplification and may be utilized in analysis, as a reactor or binding partner of the resulting amplified product. In certain methods, where sufficient concentration or sequestration of the GSTP1 nucleic acid has occurred, and wherein the oligonucleotide label and methods utilized are appropriately and sufficiently sensitive, the nucleic acid may be directly analyzed, with the presence of, or presence of a particular label indicative of the result and diagnostic of the GSTP1 genotype. After the labeled oligonucleotide or primer has had an opportunity to react with sites within the sample, the resulting product may be examined by known techniques, which may vary with the nature of the label attached. The label utilized may be radioactive or non-radioactive, including fluorescent, colorimetric or enzymatic. In addition, the label may be, for instance, a physical or antigenic tag which is characterized by its activity or binding.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein. Fab and F(ab')$_2$ portions of antibody molecules can be prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

In its broadest aspect, the present invention extends to the utilization of the GSTP1 genotype in diagnostic assays, kits and methods for determining the GSTP1 genotype thereby providing a means to determine the susceptibility to autism in a subject. Diagnostic assays, kits and methods incorporating the determination of the GSTP1 genotype of a subject are provided herein, thereby providing a means to determine the likelihood of or susceptibility to autism in a subject.

Accordingly, it is a principal object of the present invention to provide a method for identifying an individual that is genetically inclined to develop autism or autistic disease.

It is a further object of the present invention to provide a method for identifying an individual that is genetically inclined to have offspring having autistic disease.

The genotype of GSTP1 in a mother is particularly relevant in determining likelihood of, assessing susceptibility to, or assisting in clinical diagnosis of autism and autistic disease in her child, children or offspring. Specifically, in evaluating or determining appropriate management, prevention, alleviation, or therapy for autism in a fetus, for instance, the determination of GSTP1 maternal genotype, the expression or activity of GSTP1 in the mother and, thereby, the relative oxidative stress in a mother and her fetus, is relevant and useful. Further, GSTP1 genotype and susceptibility to or likelihood of autism is relevant in carrier testing and prenatal diagnosis. GSTP1 genotype and oxidative stress as a teratogenic influencer is relevant in prenatal management if a pregnant woman. While the GSTP1 alleles *A, *B, *C and *D are known and recognized polymorphic alleles of GSTP1, additional alleles, variants, mutations or alteration likely exist in the population, can be determined and evaluated by the skilled artisan, and may be similarly associated as a maternal teratogenic allele resulting in increased susceptibility of autism in a fetus.

In determining the genotype, the GSTP1 alleles *A, *B, *C and *D are determined. Genotyping the presence of the Ile105Val and/or Ala114Val alleles is relevant in determining susceptibility to or likelihood of having an autistic child. The GSTP1*A allele 313A/341C, in particular, is enriched in the mothers of autistic individuals. GSTP1 genotype may be determined by any means or methods known in the art, including but not limited to genomic Southern blotting, chromosome analysis, sequencing, RNA analysis, expression analysis, and amplification technologies such as PCR.

The assays and methods of the present invention broadly and generally include and incorporate the following steps in determining the GSTP1 genotype of an individual: (a) isolation of nucleic acid from the individual; (b) amplification of GSTP1 nucleic acid or genomic sequence; and (c) analysis of the GSTP1 nucleic acid or genomic sequence. The step (b) may be performed utilizing any method of amplification, including polymerase chain reaction (PCR), ligase chain reaction (Barany, F. (1991) Proc. Natl. Acad. Sci. 88:189-193), rolling circle amplification (Lizardi, P. M. et al (1998) Nature Genetics 19:225-232), strand displacement amplification (Walker, G. T. et al (1992) Proc. Natl. Acad. Sci. 89:392-396) or alternatively any means or method whereby concentration or sequestration of sufficient amounts of the GSTP1 nucleic acid for analysis may be obtained.

In a further embodiment of this invention, commercial test kits suitable for use by a medical specialist may be prepared to determine GSTP1 genotype, and thereby determine the specific genotype or the presence or absence of GSTP1 in an individual patient.

Accordingly, a test kit may be prepared for determining the GSTP1 genotype of an individual, whereby the GSTP1 genotype is determined, and in a particular embodiment the sequence of GSTP1 is determined. The test kit may include the PCR amplification of the nucleic acid, particularly RNA encoding or the genomic region, of GSTP1. In an additional embodiment, the RNA or genomic encoding region of GSTP1 is amplified and its characteristic sequence is determined by assessing susceptibility of the PCR product to cleavage with a particular restriction enzyme or a set of restriction enzymes. In a further embodiment, specific primer sets are utilized in amplification of the nucleic acid region of GSTP1 and the presence or absence of PCR product with the specific primer sets is evaluated in determining the GSTP1 genotype.

The DNA samples from the persons tested may be obtained from any source including blood, a tissue sample, amniotic fluid, a chorionic villus sampling, cerebrospinal fluid, and urine.

Various investigators have assessed GSTP1 genotype for association or correlation with diseases or conditions, including cancer, immune system function, chemotherapy detoxification, asthma, and lung conditions (Harries, L W et al (1997) Carcinogenesis 18(4):641-644; Yokomizo A et al (2007) Int J Urology 14(6):500-504; Aynacioglu A S et al (2003) Br J Clin Pharmacol 57(2):213-217; Watson M A et al (1998) Carcinogenesis 19(2):275-280). These investigators utilized PCR-RFLP and/or direct sequencing methods for GSTP1 genotype analysis and report same.

Any of various methods may be used to characterize the GSTP1 genotype of an individual in accordance with the invention. As above noted, the sequences of human GSTP1 and GSTP1 of other species (nucleic acid and amino acid) are known and public. The skilled artisan can readily design probes, primers, oligonucleotides for determining GSTP1 genotype, and can format or utilize tests or assays based thereon to determine GSTP1 genotype. The tests may utilize PCR, other amplification techniques, allele-specific probes or oligonucleotides, restriction analysis including RFLP analysis, sequencing or such other methods as known or devised. GSTP1 genotype of the pregnant mother or woman, the father, other relatives, siblings (autism affected or unaffected), and/or the fetus can be thus determined by the skilled artisan. The genotype of other genes involved in oxidative stress may also be determined and the results combined with GSTP1 genotype to provide additional information and further susceptibility determinations.

The Example herein provides use of an exemplary PCR-RFLP method for determining GSTP1 genotype. In the method demonstrated herein the primers used for determining the Ile 105 Val (A313G) polymorphisms were:

```
5'-CTCTATGGGAAGGACCAGCAGGAG-3'    (SEQ ID NO: 1)

5'-CAAGCCACCTGAGGGGTAAGG-3'       (SEQ ID NO: 2)
```

The primers used for determining the Ala 114 Val (C341T) polymorphisms were:

```
5'-GTTGTGGGGAGCAAGCAGAGG-3'       (SEQ ID NO: 3)

5'-CACAATGAAGGTCTTGCCTCCC-3'      (SEQ ID NO: 4)
```

The amplified DNAs are cleaved with specific restriction enzymes. One skilled in the art can use any published, known or recognized method to design primers based on the known sequences of GSTP1. These primers or probes may be used in methods including PCR methods, SSCP methods, RFLP methods, sequencing methods, allele specific oligonucleotides, etc.

In an additional alternative PCR method for the GSTP1 Ile105Val (A313G) allele, PCR was performed using the following Exon 5 primers:

```
forward: 5'-GTAGTTTGCCCAAGGTCAAG-3'    (SEQ ID NO: 5)

reverse: 5'-AGCCACCTGAGGGGTAAG-3'      (SEQ ID NO: 6)
```

PCR was performed using the following Exon 6 primers for the GSTP1 Ala114Val (C341T) allele:

```
forward:
5'-GGGAGCAAGCAGAGGAGAAT-3'        (SEQ ID NO: 7)

reverse:
5'-CAGGTTGTAGTCAGCGAAGGAG-3'      (SEQ ID NO: 8)
```

Sample DNA was added to a mix of 25 pmol of the primers, 200 µM deoxynucleoside triphosphates, 1 U of Taq polymerase (Promega Corp, Madisoin, Wis.), 1.6 mM $MgCl_2$, and a PCR buffer containing 16 mM $(NH_4)_2 SO_4$, 50 mM B-mercaptoethanol, 6.8 µM EDTA, 67 mM tris (pH 8.8) and 80 µg/ml BSA in a final volume of 30 µl. Following initial denaturation at 94° C. for 3 min, five cycles of PCR were carried out (cycle 1: 94° C. for 15 s, 64° C. for 30 s, 72° C. for 60 s) in which the annealing temperature decreased by 1° C. each cycle. This was followed by 25 cycles of amplification at 94° C. for 15 s, 59° C. for 30 s and 72° C. for 1 min. Following PCR, the entire sample was digested for 2 hours at 37° C. with restriction enzyme. The amplified nucleotide 313 region nucleic acid is cleaved with restriction enzyme Alw26I, and the amplified nucleotide 341 region nucleic acid is cleaved with restriction enzyme AciI (See Watson, M A et al (1998) Carcinogenesis 19(2):275-280).

Also, Ballerini et al have reported an improved real-time PCR method for GSTP1 complete genotyping, which implements fluorescence resonance energy transfer with a Light-Cycler instrument for analysis (Ballerini S, et al (2003) Clinica Chimica Acta 329(1-2):127-132). This method provides and automated methodology suitable for large-scale population analyses.

In a particular aspect of the invention, the GSTP1 genotype assessment is one component in a multi marker diagnostic test for autism, autistic disorders, or other neurodevelopmental disorders. In one aspect, the GSTP1 genotype is determined in conjunction with other gene markers related to oxidative stress or inflammation or other indicators of oxidative stress. Assays, methods or kits are contemplated which incorporate additional oxidative stress, inflammation, autism biomarkers or genetic markers, which may collectively with GSTP1 provide information as to susceptibility to, prevalence for, or diagnosis of autism.

Autism is a neurodevelopmental syndrome defined by deficits in social reciprocity and communication and by unusual repetitive behaviors. Although an underlying genetic predisposition is well recognized, the etiology of autism is currently unknown. Various markers, mutations, and chromosome deletions have been investigated or reported for association with and relevance for autism disease. Any subset or combination thereof may be combined with or assessed in conjunction with GSTP1 of the present invention in determining susceptibility to, assessing, or diagnosing autism disease or disorders. These include genes which act in conjunction with or in pathways associated with glutathione-S transferase or genes of distinct and unrelated pathways or any combination(s) thereof. The skilled artisan can determine, based on their knowledge of genetic correlation, disease association, statistical assessment etc those genes or other biomarkers which are relevant and significant, particularly and including in combination with GSTP1.

Deletions of various chromosomes, including chromosomes 2, 7, 15, 17, 22 and X have been noted to be associated with autism (Ashley-Koch A et al (1999) Genomics 61:227-236; Casas K A et al (2004) Am J Med Genet 130:331-339; Wassink T H et al (2005) Am J Hum Genet 136:36-44; Fine S E et al (2005) J Atism Dev Disord 35:461-470). Various reviews on genetics of autism set out candidate chromosome deletions, genes, and mutations for correlation with autism disorders or as prevalence or susceptibility markers (Freitag, C M (2007) Molecular Psychiatry 12:2-22; Gillberg C et al (1998) J Autism Dev Disorder 28:415-425; Lauristen M et al (1999) J Child Psychol Pschiatry 40:335-345; Vortsman J A (2006) Molec Psychiatry 11:1-18, 28; Folstein S E (2001) Nat Rev Genet 2:943-955).

Certain neurodevelopmental genes, neurotransporter or neuroreceptor genes have been reported as autism markers. These include reelin, engrailed-2, serotonin inn transporter, neuroligins, (neuroligins 1, 3, and 4), neurexin 1, GABA receptor gene complex (Ylisaukko-Oja T et al (2005) Eur J Hum Genet 13:1285-1292; Buxbaum J D et al (2002) Mol Psychiatry 7(3):311-316). The more recent increase in prevalence suggests that genetically determined vulnerability to environmental exposure might contribute causatively to autism. Investigators have performed family-based association studies of polymorphisms in genes involved in genes relevant to metabolism of or resistance (or sensitivity) to toxic environmental agents in metal-regulatory transcription factor 1(MTF1), a multispecific organic anion transporter (ABCC1), proton-coupled divalent metal ion transporters (SLC11A3 and SLC11A2), and paraoxonase 1 (PON1) genes in autistic disorder families (Serajee FJ et al (2004) J Child Neurol 19(6):413-7). Clock gene anomalies have been suggested as causative factors in autism and may be involved in the etiology of autistic disorder. Problems in sleep, memory and timing are all characteristics of autistic disorder and aspects of sleep, memory and timing are each clock-gene-regulated in other species. Association of Per1 and Npas2 with autism has been reported (Nicholas B et al (2007) Mol Psychiatry 12(6):581-92).

The present invention provides for the use of the nucleic acids, specifically those of GSTP1, of the present invention (as well as other nucleic acids which can be used to identify DNA polymorphisms, mutations, or alleles of the GST genes or other genes or markers involved in or indicating oxidative stress) in the methods of the present invention for monitoring, managing, identifying, diagnosing, preventing and/or treating individuals, including pregnant women and their fetus(es).

In methods of estimating the susceptibility due to genetic and/or environmental factors for an individual to have or to develop autism or to have offspring that develop autism, and for the corresponding methods for determining GSTP1 allele genotype and monitoring oxidative stress in a pregnant woman, the present invention provides a step of analyzing nucleic acids and/or proteins, including GSTP1 from biological samples. In one particular embodiment, the assaying for the presence of various GSTP1 alleles is included as part of this analysis. This or these genetic variant(s) of GSTP1 become(s) a genetic variable for susceptibility to autism and a teratogenic allele(s) for autism susceptibility.

The present invention also provides methods of estimating the genetic susceptibility of an individual to have or to develop an autistic disorder and/or for having offspring that develop an autistic disorder. One such embodiment comprises collecting a biological sample from one or more participants. The participant may be either the individual or a blood relative of the individual. The participant may be a pregnant woman. The participants may be a pregnant woman and her fetus. The participants may include the pregnant woman's parents and/or the father of the fetus. The biological sample contains nucleic acids and/or proteins of the participant. The nucleic acids and/or proteins from the biological sample are analyzed resulting in a partial or full genotype for the alleles of the gene GSTP1, optionally including the alleles of other genes involved in or associated with a prevalence or susceptibility to autism or associated with or relevant to oxidative stress. The partial or full genotype forms a dataset of teratogenic alleles for the participant.

Dietary and epidemiological information for environmental explanatory variables for the participant(s) may also be obtained and used to form a dataset of environmental explanatory variables for the participant(s). The datasets of genetic explanatory variables and the dataset of environmental explanatory variables are added to a genetic and environmental reference dataset forming a combined genetic and environmental dataset. A model may be formulated comprising the genetic and environmental explanatory variables obtained from the participant(s). The combined genetic and environmental dataset is then analyzed and a predicted probability for the individual for having and/or developing autism and/or for having offspring that develop autism is determined. The genetic and environmental susceptibility of an individual to have or to develop autism and/or have offspring that develop autism is estimated. Any of known or standard methods for analyzing the combined dataset may be used to determine or assess susceptibility to autism or a related disorder. In an embodiment, analyzing the combined genetic and environmental dataset is performed by binary linear regression. In another embodiment the model is modified by adding or subtracting one or more genetic and/or environmental explanatory variables and the combined genetic and environmental dataset is re-analyzed preferably, by binary logistic regression. A model can then be chosen that best fits the data. This can be accomplished by testing the model for goodness of fit. Exemplary such methods and models are provided and described in U.S. Pat. Nos. 6,210,950 and 6,912,492, which are incorporated herein by reference in their entirety.

The skilled artisan can determine the appropriate methods, and models, given his knowledge and the statistical and analysis methods known and available.

It is further contemplated by the present invention to provide methods that include the testing for genetic mutations in individual genes associated with glutathione s-transferase, particularly GSTP1, and/or in individual combinations of such genes. In addition, all possible combinatorials, and permutations of such genes including a constellation comprising all of the genes involved in antioxidant enzymes and oxidative stress is envisioned by the present invention. Alternatively, a constellation of genes in which any one or more genes can be excluded from those tested is also contemplated by the present invention. Thus all of such possible constellations are envisioned by, and are therefore part of the present invention.

The present invention also provides for the use of the nucleic acids of GSTP1 of the present invention in the methods of the present invention for identifying, diagnosing, modulating, monitoring, preventing and/or treating a individuals with autism or a mother and her fetus determined to have a possible or suspected prevalence for autism.

In conjunction with the characterization of the GSTP1 genotype, particularly in combination with the identification of the GSTP1*A allele, in a pregnant woman, and the recognized increased risk of having an autistic child, the levels of oxidative stress in the pregnant woman and/or in the fetus may be assessed and monitored during pregnancy. Methods and assays as well as suitable markers for assessing and monitoring oxidative stress are recognized and known in the art. For instance, levels of nitric oxide, nitrite concentrations, thiobarbituric acid reactive substances, and/or xanthane oxidase activity may be measured. Levels of endogenous antioxidants such as Vitamin C, Vitamin E, Vitamin A, zinc, and selenium, including in plasma or RBCs may be measured. Urinary excretion of 8-isoprostane (8-iso-PGF$_{2\alpha}$), a lipid peroxidation biomarker, may be monitored. Ming et al has demonstrated increased excretion of 8-isoprostane in autism patients (Ming, X, et al (2005) Prostaglandins, Leukotrienes and Essential Fatty Acids 73:379-384). Excretion of 8-hydroxy-2-deoxyguanosine (8-OHdG), a biomarker of DNA hydroxylation and indicator of oxidative damage to DNA, may be determined. Commercial ELISA kits are available for 8-iso-PGF$_{2\alpha}$ (Oxford Biochemicals, Midland, Mich.) and 8-OHdG (Genox Corporation, Baltimore, Md.). In addition, the levels of pro-inflammatory cytokines such as TNF-α, IL-1β, and IL-6 may be measured in monitoring stress.

In addition to, and in conjunction with, monitoring oxidation stress, the at risk pregnant woman and/or the fetus or child may be treated to reduce oxidation stress or reduce the component free radicals and teratogens associated with oxidation stress.

In one aspect of the invention, a pregnant woman diagnosed with the GSTP1*A allele and with enhanced probability for delivering an autistic child is managed therapeutically to reduce oxidative stress. Further, upon delivery, the child/offspring may be therapeutically managed to reduce oxidative stress.

Various methods, agents, compounds, and therapies may be used to reduce oxidative stress, and/or act as antioxidants, in the pregnant woman or her fetus or child. Antioxidant administration, such as high-dose Vitamin C or carnosine may be used (Dolske, M C et al (1993) Prog Neuro-Psychopharmacol Biol Psychiatr 17:765-774; Chez, M G et al (2002) J Child Neural 17:833-837). Supplementation with betaine and folinic acid or melatonin may be effective. The pregnant woman, fetus, or child may be treated with glutathione (GSH) or N-acetyl cysteine (NAC). Ubiquinone (coenzyme Q), quercetin, and/or phenolic compounds such as phytoestrogens, flavonoids, and phenolic acid, may have antioxidant effects. Trace elements that are components of antioxidant enzymes such as selenium, copper, zinc, and manganese may be supplemented. Various foods may also act as natural antioxidants such as tomatoes, citrus fruits, carrots, green tea or oolong tea. Other lifestyle changes and stress management techniques may also be implemented. The skilled artisan or medical individual will be familiar with the recognized and emerging modalities/therapies, supplements, compounds, agents which are suitable or applicable for reducing or managing oxidative stress.

Based on the additional function of GSTP1 in regulation of JUN N-terminal kinase (JNK), a mitogen-activated protein kinase (MAPK) and stress kinase, these kinases may also be assessed and utilized in evaluating and managing susceptibility to autism in a fetus or child. Further, JNK and/or MAPK modulators may be utilized in modulating the fetus' risk and susceptibility to autism, alone or in combination with management and therapy of oxidative stress.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

This Example demonstrates that the GSTP1*A haplotype was significantly more frequently transmitted to mothers of individuals with AD in maternal trios (Table 2), suggesting that it may be acting in mothers during pregnancy to contribute to the phenotype of autism in the fetus. The combined haplotype and genotype analyses suggest that the GSTP1-313 genotype alone had determined the observed haplotype effect. Thus the GSTP1-313*A allele may be acting as a teratogenic allele[2,4,51].

Action of a GSTP1 polymorphic variant in the mother, possibly during pregnancy, to affect her offspring may not be unprecedented. A recent study found evidence that the same GSTP1 polymorphisms in mothers were significantly correlated with lung function in their asthmatic children, an effect that was independent of transmission of alleles to the child suggesting action during pregnancy. Interestingly, asthma is a disorder in which oxidative stress plays a role[52] and in which isoprostanes have been implicated[53] as in autism[30,31]. Although we did not have information about maternal asthma in our study, a recent study reported a greater than two-fold increased risk of autism spectrum disorder in offspring if maternal diagnoses of asthma and allergies were recorded during the second trimester of pregnancy[54].

At least 15 other examples of the action of teratogenic alleles have been reported[2,4,4,51] involving at least 12 different alleles. Interestingly, one of these[2] was a GST, the GSTT1*0 allele, implicated as a possible teratogenic allele for orofacial clefting; the interaction of maternal deletion of GSTT1, that detoxifies products of cigarette smoke, with a maternal environmental effect, i.e., smoking, was associated with increased risk of having a child with oral clefting[6].

The present study is, to our knowledge, only the second to document action of a teratogenic allele or haplotype by the stringent case-parent study design[1] and the first for autism. Although TDT is robust against population stratification, the unconditional logistic regression used in this study can be affected by stratification. The permutation testing included here is considered to give results more robust to population stratification.

GSTP1 has a role in preventing and controlling oxidative stress, and oxidative stress has been linked to AD as discussed earlier. Interestingly both thalidomide[13,18] and valproic acid[55], teratogens associated with AD, induce oxidative stress[56,57] and both have been linked to depletion of GSH: valproic acid to glutathione depletion in humans[58] and thalidomide to glutathione depletion in a sensitive (rabbit) but not a resistant (rat) species[57].

GSTP1 has an additional function, regulation of JUN N-terminal kinase (JNK), a mitogen-activated protein kinase (MAPK) and stress kinase. Activation of MAPKs in response to extracellular stimuli leads to regulatory changes in a variety of cellular functions such as mitosis, differentiation, apoptosis and cell survival. Thus, MAPKs are well situated to influence brain development and differentiation, and some genes in this pathway could be candidates for autism susceptibility genes. The stress kinases are transiently activated in response to various environmental or metabolic stimuli including UV or X-irradiation, heat shock, osmotic shock or inflammatory cytokines. JNK is regulated by factors besides GSTP1, including reactive oxygen species (ROS), and changes in the redox potential. The selective and potent regulation by GSTP1 is independent of GSTP1's other functions such as detoxification and excretion of toxins and xenobiotics by conjugating them with GSH.

GSTP1 not only inhibits JNK but physically binds to it[59]. Four domains of GSTP were implicated in its regulation of JNK activation[60] through binding and/or inhibition. Interestingly, both alleles of GSTP1*A haplotype associated here with autism occur within the region contributing to binding of the GST protein to the JUN-JNK complex; GSTP1 residue 105, which contributed most or all of the haplotype effect observed, also lies within the H-site, the region where electrophilic toxins, xenobiotics or metabolites bind to GST for conjugation with GSH[40].

JNK activation and clinical therapeutic response using CNI-1493, an inhibitor of JNK and p38 MAPK activation, were reported[61] in Crohn's disease, which is an inflammatory bowel disease (IBD). A panenteric IBD-like disease has been reported in regressive AD[62]. Thus, JNK can be a therapeutic target for the IBD-like disease in AD based on the present results linking GSTP1 alleles and autism.

Also, a number of the genes reported to be associated with autism are related to MAPKs or MAPK pathways as is GSTP1. For example, both the reelin gene[63] and the APOE[64] gene have been associated with autism and both proteins competitively bind the same receptor[65,66], ApoER2. A direct molecular link between ApoER2 and the JNK signaling pathway has been demonstrated[65,66]. The finding is strengthened by a previous study in which we associated homozygosity for the GSTM1 deletion allele with AD[67]. Interestingly, GSTM1 also detoxifies xenobiotics and independently regulates two MAPKs, ASK1 and MEKK1, by binding to them.

Accordingly, screening for the GSPT1 gene and genotype can be useful in the determination of susceptibility to, monitoring, management, diagnosis, and treatment of autism and can also be used in genetic counseling and prenatal diagnosis, management, and care.

Participants, Materials and Methods

Families having a child diagnosed with autism were invited to participate through advertisements in the newsletter of the New Jersey Center for Outreach and Services for the Autism Community (COSAC, Ewing, N.J.). A few families were recruited through our Department of Pediatrics. Selection criteria for families were as follows: (1) participation of a proband with the clinical diagnosis of autism by their neurodevelopmental pediatrician as assessed by telephone interview with the primary caregiver; (2) clinical diagnosis of AD confirmed for each proband by the autism diagnostic Interview-revised (ADI-R) and the autism diagnostic observation schedule-generic (ADOS-G) testing[45,46]; (3) blood sampling from mother and at least one maternal grandparent. All probands were tested using both the Autism Diagnostic Interview-Revised (ADI-R) and the Autism Diagnostic Observation Schedule-Generic (ADOS-G) by a trained and certified examiner (AM) and all received the clinical diagnosis of AD by this testing.

Venous blood was collected in Vacutainers containing EDTA. The samples were either frozen immediately in cryovials at −70° C. or frozen briefly (2-3 days) at −20° C. for transport to the laboratory and prepared there. Genomic DNA was obtained from whole blood or white blood cells isolated by centrifugation. DNA extraction was done using Qiagen QIAamp DNA Blood Kits (Qiagen, Valencia, Calif.). Genomic DNA was stored at 4° C.

Genotyping of the GSTP1*A313G (Ile105Val) and *C341T (Ala114Val) polymorphisms was carried out by PCR-RFLP methods as previously described[44]. PCR was carried out in a Perkin Elmer GeneAmp 9600 thermal cycler. The polymorphism A313G was detected by PCR with the following primer pair:

```
5'-CTCTATGGGAAGGACCAGCAGGAG-3'    (SEQ ID NO: 1)

5'-CAAGCCACCTGAGGGGTAAGG-3'       (SEQ ID NO: 2)
```

The polymorphism C341T was detected by PCR with the primer pair:

```
5'-GTTGTGGGGAGCAAGCAGAGG-3'       (SEQ ID NO: 3)

5'-CACAATGAAGGTCTTGCCTCCC-3'      (SEQ ID NO: 4)
```

For GSTP1*A313G (Ile105Val), the PCR product was restricted with Alw26I; products were separated on 8% polyacrylamide gels and visualised with ethidium bromide. Digestion produced 110- and 90-bp fragments for the G allele, and a 200-bp band consistent with the PCR amplimer for the A allele, which had no Alw26I restriction site. For GSTP1*C341T (Ala114Val), the PCR product was restricted with AciI; products were separated on 8% polyacrylamide gels with 1× Tris-borate-EDM (TBE) buffer and visualised with ethidium bromide. Digestion produced approximately 120 and approximately 90 bp fragments for the C allele, and an approximately 210 bp band consistent with the PCR amplimer for the T allele, which had no AciI restriction site. The GSTP1*A haplotype is 313A/341C, GSTP1*B haplotype is 313G/341C and GSTP1*C haplotype is 313G/341T. GSTP1D, 313A/341T, is rare and did not occur in the present dataset.

The two-locus haplotypes were analyzed, with the individual genotypes examined in a secondary analysis. Haplotype frequencies were determined with maximum likelihood estimation using the expectation-minimization (EM) algorithm[47]. Association of haplotypes with AD was tested with the TDT-Phase program[48], using the EM algorithm for both uncertain haplotypes and for incomplete parental genotypes. The program fits an unconditional logistic regression using transmitted haplotypes as pseudo-cases and untransmitted haplotypes as pseudo-controls, thus modeling the haplotype relative risk[49]. Incorporating uncertain haplotypes subjects the algorithm to population stratification effects. Permutation testing, whereby the transmitted and untransmitted labels are re-assigned, gives a result more robust against population stratification.

Individual genotypes were examined with the classical transmission/disequilibrium test[50], as implemented in TDT-Phase (by specifying one genotype at a time and no EM algorithm). They were also examined by means of maximum likelihood estimation using the EM algorithm to loop over uncertain parental genotypes.

Results

GSTP1 was recently studied in autism using a family-based association study design.[42] That study included only case trios (affected individual and parents) and had negative results. In the present study, we genotyped 137 individuals in 49 families with AD for the GSTP1*G313A and GSTP1*C341T polymorphisms[43] using maternal trios (mother of individual with AD and her parents) to look for a teratogenic allele. We analyzed these single nucleotide polymorphisms and the resulting haplotypes using a haplotype-based statistical approach.

We genotyped the GSTP1*G313A and *C341T SNPs in a total of 137 members of 49 families with an AD proband. There were 49 mothers, 49 maternal grandmothers and 39 maternal grandfathers in 39 complete maternal trios and 10 incomplete maternal trios The distribution of GSTP1 haplotype frequencies (Table 1) was comparable with published frequencies[44].

TABLE 1

Estimated Haplotype Probabilities**

| Haplotypes | Components | Frequencies |
|---|---|---|
| GSTP1*A | 313A/341C | 0.71 |
| GSTP1*B | 313G/341C | 0.20 |
| GSTP1*C | 313G/341T | 0.09 |
| GSTP1*D | 313A/341T | Not observed in sample; frequency set to zero |

**Maximum likelihood estimates based on founders only.

The haplotype analysis (Table 2) demonstrated significant over transmission (p=0.0136, with p=0.0343 in permutation testing). The GSTP1*A haplotype was over transmitted to mothers, while GSTP1*B and GSTP1*C were both under transmitted. These two were under transmitted at almost the same rate. When those two rates are constrained to be equal, the odds ratio for the GSTP1*A haplotype is 1/0.375=2.67 (95% confidence interval: 1.39, 5.13).

TABLE 2

TDT-Phase Haplotype Results*

| Haplotype | Transmitted | | Not Transmitted | | Odds Rate (OR) |
| | Number | Frequency | Number | Frequency | (95% CI) |
|---|---|---|---|---|---|
| GSTP1*A | 80 | 0.82 | 61.25 | 0.63 | 1 |
| GSTP1*B | 13 | 0.13 | 25.61 | 0.26 | 0.389 (0.184, 0.819) |
| GSTP1*C | 5 | 0.05 | 11.14 | 0.11 | 0.344 (0.114, 01.039) |

Likelihood Test Statistic = 8.63, 2 df, p = 0.0136. P-value from permutation testing: p = 0.0343.
*EM algorithm used for both uncertain phase and missing genotypes.

To better understand the haplotype effect, we examined the individual genotypes. The individual genotypes (Tables 3 and 4) were not significantly over transmitted using the TDT (p=0.0608 for GSTP1-313 and p=0.3627 for GSTP1-341), although the A allele at GSTP1-313 was close to being significantly over transmitted. Testing by means of maximum likelihood estimation using the EM algorithm for missing data gave a highly significant over transmission of GSTP1-313*A (p=0.0047; p=0.0036 using permutation) while GSTP1-341 remained not significant (p=0.1049). Both loci were in Hardy-Weinberg equilibrium among maternal grandparents (p=0.3117 for 313, p=0.5963 for 341) and mothers of individuals with AD (p=0.9003 and p=0.7142, respectively).

TABLE 3

TDT of Individual Markers*

| Genotype | Transmitted | | Not Transmitted | | OR |
| | Number | Freq | Number | Freq | |
|---|---|---|---|---|---|
| GSTP1-313*A | 23 | 0.66 | 12 | 0.34 | 1 |
| GSTP1-313*G | 12 | 0.34 | 23 | 0.66 | 0.522 (0.260-1.049) |
| GSTP1-341*C | 7 | 0.64 | 4 | 0.36 | 1 |
| GSTP1-341*T | 4 | 0.36 | 7 | 0.64 | 0.571 (0.167-1.952) |

OR = Odds Ratio (95% Confidence Interval)
GSTP1-313 p = 0.0608. GSTP1-341 p = 0.3627.
*TDT-Phase with one marker at a time and with no EM algorithm yielding the classical TDT.

TABLE 4

TDT-Phase Results on Individual Markers*

| Genotype | Transmitted | | Not Transmitted | | OR |
| | Number | Freq | Number | Freq | |
|---|---|---|---|---|---|
| GSTP1-313*A | 80 | 0.82 | 61.95 | 0.63 | 1 |
| GSTP1-313*G | 18 | 0.18 | 36.05 | 0.37 | 0.387 (0.200-0.745) |
| GSTP1-341*C | 93 | 0.95 | 86.60 | 0.88 | 1 |
| GSTP1-341*T | 5 | 0.05 | 11.40 | 0.12 | 0.409 (0.137-1.216) |

OR = Odds Ratio (95% Confidence Interval)
GSTP1-313 p = 0.0047. GSTP1-341 p = 0.1049. Permutation p-value for GSTP1-313 is p = 0.0036.
*TDT-Phase with full likelihood and EM algorithm for missing genotype information Findings from the combined haplotype and genotype analyses indicated that the GSTP1-313 genotype alone had determined the observed haplotype effect. The haplotype data enabled some matings that were uninformative for classical TDT to be resolved and so enabled greater power for testing.

References (1) Doolin M T, Barbaux S, McDonnell M, Hoess K, Whitehead A S, Mitchell L E. Maternal genetic effects, exerted by genes involved in homocysteine remethylation, influence the risk of spina bifida. Am J Hum Genet 2002; 71(5):1222-1226.

(2) Johnson W G. Teratogenic Alleles and Neurodevelopmental Disorders. BioEssays 2003; 25:464-477.

(3) Doolin M T, Barbaux S, McDonnell M, Hoess K, Whitehead A S, Mitchell L E. Maternal genetic effects, exerted by genes involved in homocysteine remethylation, influence the risk of spina bifida. Am J Hum Genet 2002; 71(5):1222-1226.

(4) Johnson W G, Stenroos E S, Spychala J, Buyske S, Chatkupt S, Ming X. A New 19 bp Deletion Polymorphism in Intron-1 of Dihydrofolate Reductase (DHFR)—A Risk Factor for Spina Bifida Acting in Mothers During Pregnancy? Am J Med Genet 2004; 124A(4):339-345.

(5) O'Leary V B, Parle-McDermott A, Molloy A M, Kirke P N, Johnson Z, Conley M et al. MTRR and MTHFR polymorphism: link to Down syndrome? Am J Med Genet 2002; 107(2): 151-155.

(6) van Rooij I A, Wegerif M J, Roelofs H M, Peters W H, Kuijpers-Jagtman A M, Zielhuis G A et al. Smoking, genetic polymorphisms in biotransformation enzymes, and nonsyndromic oral clefting: a gene-environment interaction. Epidemiol 2001; 12(5):502-507.

(7) American Psychiatric Association. Diagnostic and Statistical Manual of Mental Disorders. Fourth ed. Washington, D.C.: American Psychiatric Association, 1994.

(8) Rapin I. Autism. N Engl J Med 1997; 337:97-104.

(9) Muhle R, Trentacoste S V, Rapin I. The genetics of autism. Pediatrics 2004; 113(5):e472-e486.

(10) Szatmari P. The causes of autism spectrum disorders. BMJ 2003; 326(7382):173-174.

(11) Lawler C P, Croen L A, Grether J K, Van de Water J. Identifying environmental contributions to autism: provocative clues and false leads. Ment Retard Dev Disabil Res Rev 2004; 10(4):292-302.

(12) Rodier P M, Ingram J L, Tisdale B, Nelson S, Romano J. Embryological origin for autism: developmental anomalies of the cranial nerve motor nuclei. J Comp Neurol 1996; 370:247-261.

(13) Stromland K, Nordin V, Miller M, Akerstrom B, Gillberg C. Autism in thalidomide embryopathy: a population study. Dev Med Child Neurol 1994; 36:351-356.

(14) Piven J, O'Leary D. Neuroimaging in autism. Child Adol Psychiatr Clin N A 1999; 6:305-323.

(15) Casanova M F, Buxhoeveden D, Gomez J. Disruption in the inhibitory architecture of the cell minicolumn: implications for autisim. Neuroscientist 2003; 9(6):496-507.

(16) Casanova M F, Buxhoeveden D P, Switala A E, Roy E. Minicolumnar pathology in autism. Neurology 2002; 58(3):428-432.

(17) Nelson K B, Grether J K, Croen L A, Dambrosia J M, Dickens B F, Jelliffe L L et al. Neuropeptides and neurotrophins in neonatal blood of children with autism or mental retardation. Ann Neurol 2001; 49(5):597-606.

(18) Rodier P M, Ingram J L, Tisdale B, Croog V J. Linking etiologies in humans and animal models: studies of autism. Reprod Toxicol 1997; 11:417-422.

(19) Alsdorf R, Wyszynski D F. Teratogenicity of sodium valproate. Expert Opin Drug Saf 2005; 4(2):345-353.

(20) Leonard H, de Klerk N, Bourke J, Bower C. Maternal Health in Pregnancy and Intellectual Disability in the Offspring: A Population-Based Study. Ann Epidemiol 2005; 16(448):454.

(21) Jones M B, Palmour R M, Zwaigenbaum L, Szatmari P. Modifier effects in autism at the MAO-A and DBH loci. Am J Med Genet B Neuropsychiatr Genet 2004; 126(1): 58-65.

(22) Shattuck P T. The contribution of diagnostic substitution to the growing administrative prevalence of autism in US special education. Pediatrics 2006; 117(4):1028-1037.

(23) Jamain S, Betancur C, Quach H, Philippe A, Fellous M, Giros B et al. Linkage and association of the glutamate receptor 6 gene with autism. Mol Psychiatry 2002; 7(3): 302-310.

(24) Daniels W W, Warren R P, Odell J D, Maciulis A, Burger R A, Warren W L et al. Increased frequency of the extended or ancestral haplotype B44-SC30-DR4 in autism. Neuropsychobiology 1995; 32:120-123.

(25) Chauhan A, Chauhan V. Oxidative stress in autism. Pathophysiology 2006; 13(3):171-181.

(26) James S J, Cutler P, Melnyk S, Jernigan S, Janak L, Gaylor D W et al. Metabolic biomarkers of increased oxidative stress and impaired methylation capacity in children with autism. Am J Clin Nutr 2004; 80(6):1611-1617.

(27) James S J, Melnyk S, Jernigan S, Cleves M A, Halsted C H, Wong D H et al. Metabolic endophenotype and related genotypes are associated with oxidative stress in children with autism. Am J Med Genet B Neuropsychiatr Genet 2006; in press.

(28) Coles B F, Kadlubar F F. Detoxification of electrophilic compounds by glutathione S-transferase catalysis: determinants of individual response to chemical carcinogens and chemotherapeutic drugs? BioFactors 2003; 17(1-4): 115-130.

(29) Li Y, Wei G, Chen J. Glutathione: a review on biotechnological production. Appl Microbiol Biotechnol 2004; 66(3):233-242.

(30) Ming X, Stein T P, Brimacombe M, Johnson W G, Lambert G H, Wagner G C. Increased excretion of a lipid peroxidation biomarker in autism. Prostaglandins Leukot Essent Fatty Acids 2005; 73(5):379-384.

(31) Yao Y, Walsh W J, McGinnis W R, Pratico D. Altered vascular phenotype in autism: correlation with oxidative stress. Arch Neurol 2006; 63(8):1161-1164.

(32) Hayes J D, Strange R C. Glutathione S-transferase polymorphisms and their biological consequences. Pharmacology 2000; 61(3):154-166.

(33) Hayes J D, McLellan L I. Glutathione and glutathione-dependent enzymes represent a coordinately regulated defence against oxidative stress. Free Radic Res 1999; 31(4):273-300.

(34) Kauffman F C. Xenobiotic metabolism by the liver. In: Sipes I G, McQueen C A, Gandolfi A J, McCuskey R S, Earnest D L, editors. Comprehensive Toxicology. Oxford, N.Y.: Pergamon, 1997: 73-95.

(35) Ahmed A E, Aronson J, Jacob S. Induction of oxidative stress and TNF-alpha secretion by dichloroacetonitrile, a water disinfectant by-product, as possible mediators of apoptosis or necrosis in a murine macrophage cell line (RAW). Toxicol Vitr 2000; 14(3):199-210.

(36) Hayes J D, Flanagan J U, Jowsey I R. Glutathione Transferases. Annu Rev Pharmacol Toxicol 2005; 45:51-88.

(37) Forsberg L, de Faire U, Morgenstern R. Low yield of polymorphisms from EST blast searching: analysis of genes related to oxidative stress and verification of the P197L polymorphism in GPX1. Hum Mutat 1999; 13(4): 294-300.

(38) Zimniak P, Nanduri B, Pikula S, Bandorowicz-Pikula J, Singhal S S, Srivastava S K et al. Naturally occurring human glutathione S-transferase GSTP1-1 isoforms with isoleucine and valine in position 104 differ in enzymic properties. Eur J Biochem 1994; 224(3):893-899.

(39) Hu X, Xia H, Srivastava S K, Herzog C, Awasthi Y C, Ji X et al. Activity of four allelic forms of glutathione S-transferase hGSTP1-1 for diol epoxides of polycyclic aromatic hydrocarbons. Biochem Biophys Res Commun 1997; 238 (2):397-402.

(40) Johansson A S, Stenberg G, Widersten M, Mannervik B. Structure-activity relationships and thermal stability of human glutathione transferase P1-1 governed by the H-site residue 105. J Mol Biol 1998; 278(3):687-698.

(41) Sundberg K, Johansson A S, Stenberg G, Widersten M, Seidel A, Mannervik B et al. Differences in the catalytic efficiencies of allelic variants of glutathione transferase P1-1 towards carcinogenic diol epoxides of polycyclic aromatic hydrocarbons. Carcinogenesis 1998; 19(3):433-436.

(42) Matsui A, Ikeda T, Enomoto K, Hosoda K, Nakashima H, Omae K et al. Increased formation of oxidative DNA damage, 8-hydroxy-2'-deoxyguanosine, in human breast cancer tissue and its relationship to GSTP1 and COMT genotypes. Cancer Lett 2000; 151(1):87-95.

(43) Serajee F J, Nabi R, Zhong H, Huq M. Polymorphisms in xenobiotic metabolism genes and autism. J Child Neurol 2004; 19(6):413-417.

(44) Menegon A, Board P G, Blackburn A C, Mellick G D, Le Couteur D G. Parkinson's disease, pesticides, and glutathione transferase polymorphisms. Lancet 1998; 352 (9137):1344-1346.

(45) Lord C, Rutter M, Le Couteur A. Autism Diagnostic Interview-Revised: a revised version of a diagnostic interview for caregivers of individuals with possible pervasive developmental disorders. J Autism Dev Disord 1994; 24(5):659-685.

(46) Lord C, Risi S, Lambrecht L, Cook E H, Jr., Leventhal B L, DiLavore P C et al. The autism diagnostic observation schedule-generic: a standard measure of social and communication deficits associated with the spectrum of autism. J Autism Dev Disord 2000; 30(3):205-223.

(47) Excoffier L, Slatkin M. Maximum-likelihood estimation of molecular haplotype frequencies in a diploid population. Mol Biol Evol 1995; 12(5):921-927.

(48) Dudbridge F. Pedigree disequilibrium tests for multilocus haplotypes. Genet Epidemiol 2003; 25(2):115-121.

(49) Terwilliger J D, Ott J. A haplotype-based 'haplotype relative risk' approach to detecting allelic associations. Hum Hered 1992; 42(6):337-346.

(50) Spielman R S, McGinnis R E, Ewens W J. Transmission test for linkage disequilibrium: The insulin gene region and insulin-dependent diabetes mellitus (IDDM). Am J Hum Genet 1993; 52:506-516.

(51) Johnson W G. The DNA Polymorphism-Diet-Cofactor-Development Hypothesis and the Gene-Teratogen Model for schizophrenia and other developmental disorders. Am J Med Genet (Neuropsychiatr Genet) 1999; 88:311-323.

(52) Carroll W D, Lenney W, Child F, Strange R C, Jones P W, Fryer A A. Maternal glutathione S-transferase GSTP1 genotype is a specific predictor of phenotype in children with asthma. Pediatr Allergy Immunol 2005; 16(1):32-39.

(53) Zanconato S, Carraro S, Corradi M, Alinovi R, Pasquale M F, Piacentini G et al. Leukotrienes and 8-isoprostane in exhaled breath condensate of children with stable and unstable asthma. J Allergy Clin Immunol 2004; 113(2): 257-263.

(54) Croen L A, Grether J K, Yoshida C K, Odouli R, Van de WJ. Maternal autoimmune diseases, asthma and allergies, and childhood autism spectrum disorders: a case-control study. Arch Pediatr Adolesc Med 2005; 159(2):151-157.

(55) Narita N, Kato M, Tazoe M, Miyazaki K, Narita M, Okado N. Increased monoamine concentration in the brain and blood of fetal thalidomide- and valproic acid-exposed rat: putative animal models for autism. Pediatr Res 2002; 52(4):576-579.

(56) Parman T, Wiley M J, Wells P G. Free radical-mediated oxidative DNA damage in the mechanism of thalidomide teratogenicity. Nat Med 1999; 5(5):582-585.

(57) Hansen J M, Harris K K, Philbert M A, Harris C. Thalidomide modulates nuclear redox status and preferentially depletes glutathione in rabbit limb versus rat limb. J Pharmacol Exp Ther 2002; 300(3):768-776.

(58) Cengiz M, Yuksel A, Seven M. The effects of carbamazepine and valproic acid on the erythrocyte glutathione, glutathione peroxidase, superoxide dismutase and serum lipid peroxidation in epileptic children. Pharmacol Res 2000; 41(4):423-425.

(59) Adler V, Yin Z, Fuchs S Y, Benezra M, Rosario L, Tew K D et al. Regulation of JNK signaling by GSTp. EMBO J 1999; 18(5):1321-1334.

(60) Adler V, Pincus M R. Effector peptides from glutathione-S-transferase-pi affect the activation of jun by jun-N-terminal kinase. Ann Clin Lab Sci 2004; 34(1):35-46.

(61) Hommes D, van den B B, Plasse T, Bartelsman J, Xu C, Macpherson B et al. Inhibition of stress-activated MAP kinases induces clinical improvement in moderate to severe Crohn's disease. Gastroenterology 2002; 122(1):7-14.

(62) Balzola F, Barbon V, Repici A, Rizzetto M, Clauser D, Gandione M et al. Panenteric IBD-like disease in a patient with regressive autism shown for the first time by the wireless capsule enteroscopy: another piece in the jigsaw of this gut-brain syndrome? Am J Gastroenterol 2005; 100(4):979-981.

(63) Persico A M, D'Agruma L, Maiorano N, Totaro A, Militerni R, Bravaccio C et al. Reelin gene alleles and haplotypes as a factor predisposing to autistic disorder. Mol Psychiatry 2001; 6(2):150-159.

(64) Persico A M, D'Agruma L, Zelante L, Militerni R, Bravaccio C, Schneider C et al. Enhanced APOE2 transmission rates in families with autistic probands. Psychiatr Genet 2004; 14(2):73-82.

(65) Stockinger W, Brandes C, Fasching D, Hermann M, Gotthardt M, Herz J et al. The reelin receptor ApoER2 recruits JNK-interacting proteins-1 and -2. J Biol Chem 2000; 275(33):25625-25632.

(66) Hoe H S, Harris D C, Rebeck G W. Multiple pathways of apolipoprotein E signaling in primary neurons. J Neurochem 2005; 93(1):145-155.

(67) Buyske S, Williams T A, Mars A E, Stenroos E S, Ming S X, Wang R et al. Analysis of case-parent trios at a locus with a deletion allele: association of GSTP1 with autism. BMC Genet 2006; 7(1):8.

(68) Watson, M A, Stewart, R K, Smith, G B J, Massey, T E and Bell, D A. Human Glutathione S-transferase P1 polymorphisms: relationship to lung tissue enzyme activity and population frequency distribution. Carcinogenesis 1998; 19(2):275-280.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A method for identifying a female individual with a greater likelihood of having offspring with an autistic disorder comprising the steps of:
   (a) collecting a biological sample from a female individual or a blood relative of the individual; wherein the biological sample contains nucleic acids;
   (b) performing PCR on said nucleic acids; and
   (c) assaying said nucleic acids for glutathione S-transferase P1 (GSTP1) polymorphisms GSTP1*G313A and GSTP1*C341T; and
   (d) identifying said nucleic acids for said GSTP1 polymorphisms;
   wherein the step (b) performing PCR on said nucleic acids further includes utilizing at least one primer, wherein said primer is selected from the group consisting of SEQ ID NOS: 1-8 wherein the presence of said GSTP1*G313A polymorphism and said GSTP1*C341T polymorphism identifies said female individual as having a greater likelihood of having offspring with an autistic disorder.

2. The method of claim 1 wherein the step c) assaying said nucleic acids for glutathione S-transferase P1 (GSTP1) polymorphisms further includes utilizing at least one probe, wherein said probe is a labeled probe and provides a signal upon the presence of a GSTP1*G313A polymorphism and a GSTP1*C341T polymorphism.

3. The method of claim 1 wherein said female individual is pregnant.

4. A method of identifying a female individual with a greater likelihood of having offspring with an autistic disorder comprising the steps of:
   (a) collecting a biological sample from a female individual; wherein the biological sample contains nucleic acids of said female individual; and
   (b) isolating said nucleic acids from the biological sample;
   (c) performing a nucleic acid hybridization assay on said nucleic acids using a first probe to detect GSTP1*G313A and a second probe to detect GSTP1*C341T polymorphisms; and
   (d) identifying said nucleic acids for said GSTP1*G313A and GSTP1*C341T polymorphisms;
   wherein said first probe is selected from the group consisting of SEQ ID Nos. 1, 2, 5 and 6 or said second probe is selected from the group consisting of SEQ ID Nos. 3, 4, 7, and 8; wherein the presence of said GSTP1*G313A polymorphism and said GSTP1*341T identifies said female individual as having a greater likelihood of having offspring with an autistic disorder.

5. The method of claim 4, wherein said probe is a labeled probe.

6. The method of claim 4, wherein said female individual is pregnant.

* * * * *

SEQUENCE LISTING

```
<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
ctctatggga aggaccagca ggag                                          24

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
caagccacct gagggtaag g                                              21

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
gttgtgggga gcaagcagag g                                             21

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
cacaatgaag gtcttgcctc cc                                            22

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gtagtttgcc caaggtcaag                                               20

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
```

```
agccacctga ggggtaag                                                    18

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gggagcaagc agaggagaat                                                  20

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
caggttgtag tcagcgaagg ag                                               22

<210> SEQ ID NO 9
<211> LENGTH: 210
<212> TYPE: PRT
<213> ORGANISM: Homo sapiens

<400> SEQUENCE: 9
```

Met Pro Pro Tyr Thr Val Val Tyr Phe Pro Val Arg Gly Arg Cys Ala
 1               5                  10                  15

Ala Leu Arg Met Leu Leu Ala Asp Gln Gly Gln Ser Trp Lys Glu Glu
            20                  25                  30

Val Val Thr Val Glu Thr Trp Gln Glu Gly Ser Leu Lys Ala Ser Cys
        35                  40                  45

Leu Tyr Gly Gln Leu Pro Lys Phe Gln Asp Gly Asp Leu Thr Leu Tyr
    50                  55                  60

Gln Ser Asn Thr Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

Val Glu Asp Leu Arg Cys Lys Tyr Ile Ser Leu Ile Tyr Thr Asn Tyr
            100                 105                 110

Glu Ala Gly Lys Asp Asp Tyr Val Lys Ala Leu Pro Gly Gln Leu Lys
        115                 120                 125

Pro Phe Glu Thr Leu Leu Ser Gln Asn Gln Gly Gly Lys Thr Phe Ile
    130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
            180                 185                 190

Phe Leu Ala Ser Pro Glu Tyr Val Asn Leu Pro Ile Asn Gly Asn Gly
        195                 200                 205

Lys Gln
    210

```
<210> SEQ ID NO 10
<211> LENGTH: 737
```

-continued

```
<212> TYPE: DNA
<213> ORGANISM: Homo sapiens

<400> SEQUENCE: 10
ggagtttcgc cgccgcagtc ttcgccacca tgccgccta caccgtggtc tatttcccag      60
ttcgaggccg ctgcgcggcc ctgcgcatgc tgctggcaga tcagggccag agctggaagg     120
aggaggtggt gaccgtggag acgtggcagg agggctcact caaagcctcc tgcctatacg    180
ggcagctccc caagttccag gacggagacc tcaccctgta ccagtccaat accatcctgc    240
gtcacctggg ccgcacccit gggctctatg ggaaggacca gcaggaggca gccctggtgg    300
acatggtgaa tgacggcgtg gaggacctcc gctgcaaata catctccctc atctacacca    360
actatgaggc gggcaaggat gactatgtga aggcactgcc cgggcaactg aagccttttg    420
agaccctgct gtcccagaac cagggaggca agaccttcat tgtgggagac cagatctcct    480
tcgctgacta caacctgctg gacttgctgc tgatccatga ggtcctagcc cctggctgcc    540
tggatgcgtt ccccctgctc tcagcatatg tggggcgcct cagcgcccgg cccaagctca    600
aggccttcct ggcctcccct gagtacgtga acctccccat caatggcaac gggaaacagt    660
gagggttggg gggactctga gcgggaggca gagtttgcct tcctttctcc aggaccaata    720
aaatttctaa gagagct                                                    737
```